United States Patent [19]

Travis et al.

[11] 4,093,612

[45] June 6, 1978

[54] SELECTIVE REMOVAL OF ALBUMIN FROM BLOOD FLUIDS AND COMPOSITIONS THEREFORE

[75] Inventors: James Travis; Ralph Pannell, both of Athens, Ga.

[73] Assignee: Research Corporation, New York, N.Y.

[21] Appl. No.: 661,890

[22] Filed: Feb. 27, 1976

Related U.S. Application Data

[63] Continuation-in-part of Ser. No. 601,676, Aug. 4, 1975, Pat. No. 4,016,149, which is a continuation-in-part of Ser. No. 396,036, Sep. 10, 1973, abandoned.

[51] Int. Cl.$^2$ ............................ A23J 1/00; C07G 7/00
[52] U.S. Cl. ........................................ 260/122; 260/8; 260/121
[58] Field of Search ........................... 260/8, 121, 122

[56] References Cited

U.S. PATENT DOCUMENTS 4,016,149  4/1977  Travis et al. ........................ 260/122

OTHER PUBLICATIONS

Behring Inst. Mitt. 54, 30–32 (1974), Travis et al.
Clin. Chim. Acta, 49, pp. 49–52, 1973, Travis et al.
Chem. Abst., vol. 83, 1975, 24718e, Travis et al.
Chem. Abst., vol. 81, 1974, 165663d, Travis et al.

*Primary Examiner*—Howard E. Schain
*Attorney, Agent, or Firm*—Omri M. Behr

[57] ABSTRACT

Certain compositions have been prepared by the reaction of certain dyes of the class generally known as Color Index reactive dyes with certain support phases. The dyes utilized for said compositions all possess the general sulfanilido-triazidinyl-sulfoaryl group wherein the aryl groups may be phenyl or naphthyl and said general group is further bonded to aryl groups via an amino or azo linkage. It has been found that when aqueous fluids containing albumin, such as, for example, plasma or serum are passed over compositions within the scope of the present invention albumin is selectively adsorbed on said compositions without removal of other proteins present in the fluid. It has further been found that the albumin may be readily removed from the thus formed adsorbate without denaturing the albumin and leaving the solid phase dye composition in a suitable state for re-use without loss of activity.

19 Claims, No Drawings

SELECTIVE REMOVAL OF ALBUMIN FROM BLOOD FLUIDS AND COMPOSITIONS THEREFORE

The invention described herein was made in the course of work under grant or award from the Department of Health, Education and Welfare of the United States of America.

RELATED APPLICATIONS

This application is a continuation-in-part of applicant's co-pending application, Ser. No. 601,676, filed Aug. 4, 1975, now U.S. Pat. No. 4,016,149, which in turn is a continuation-in-part of their then co-pending application, Ser. No. 396,036 filed Sept. 10, 1973, now abandoned.

FIELD OF THE INVENTION

Selective fractionation of proteins in blood fluids.

DESCRIPTION OF THE PRIOR ART

It is well known that blood fluids such as plasma and serum contain many proteins which it is desirable to isolate in a pure state. Isolation procedures for such proteins are known, however, they all suffer from a common problem, namely, the presence of albumin. Albumin is the major protein constituent in plasma. Besides being a contaminant in the aforementioned procedures, it is often desirable to isolate pure albumin uncontaminated by other proteins. Thus, it would be most desirable to develop a procedure whereby albumin can be selectively removed from blood fluids without simultaneous removal of other proteins which may be present in very small quantities.

It is well known that certain proteins will bind very tightly to certain reactive dyes. It has been reported that Blue Dextran will bind tightly with lysozyme, ovalbumin, and hemoglobin when they carry net positive charge, and bovine serum albumin independent of charge. Blue Dextran is a dye generally known as Procion Blue HBS wherein the chlorine atom on the triazine moiety of the dye is replaced by the polymer Dextran being bonded to said triazine group via —O— grouping. (White and Jencks Binding of Proteins to Blue Dextran, No. 43, Biol., Abstracts, 160th National Meeting, American Chemical Society, September 14, -18, 1970). It should be noted however that Blue Dextran is water soluble. Thus, an operative procedure would involve coupling Blue Dextran to a solid substrate from which the albumin can be removed. It would be particularly desirable if, in addition to removal of the albumin in such a manner that the absorptive capacity of the substrate was not damaged, the albumin was regenerated in such way that it was not denatured.

Cuatrecasas has disclosed a method of protein purification by affinity chromatography. In the Cuatrecasas procedure insoluble materials are prepared by coupling certain large molecules containing amino groups to agarose by activating the agarose with cyanogen bromide prior to treating the activated agarose with the amino containing moiety. ( J.Biol.Chem. 245,3059,(1970).

Bohme et al (J. Chromatogr., 69, 209, (1972)) found that the condensation product of Cibacron Blue F3G-A, otherwise known as Procion Blue HBS with Dextran 2000, otherwise known as Blue Dextran 2000 (a trademarked product of Pharmacia, Uppsala, Sweden) had a high affinity for the enzyme phosphofructokinase. On the other hand, the condensation product of Dextran 2000 with Cibacron Brilliant Blue FBR-P, a dye of extremely similar structure, showed no affinity for phosphofructokinase. Neither was such activity shown when Blue Dextran was coupled with cyanogen bromide activated sepharose.

The specificity of dyes for certain polypeptides is therefore not predictable.

SUMMARY OF THE INVENTION

It has been found that certain reactive dyes when coupled to certain solid support phases provide a composition upon which albumin may be selectively adsorbed out from the presence of other proteins from substantially cell free aqueous fluids such as plasma or serum. The adsorbed albumin may be removed, in high yield, without denaturization, from said compositions and compositions may be re-utilized without loss of adsorbative capacity. The support phases which may be utilized for this purpose include agarose, more particularly sepharose, polyacrylamides, more particularly cross-linked polyacrylamide gel, and acrylic resins, more particularly anion exchange resins such as Amberlite IRC 45, containing an amino group.

These support phases are bonded to Color Index reactive dyes (hereinafter CRD) wherein the CRD has the general formula

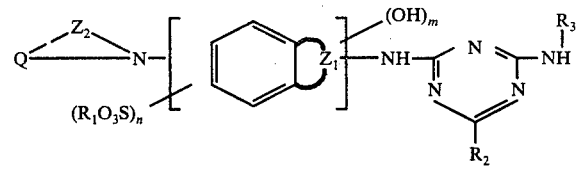

wherein $R_1$ is hydrogen, an alkali metal, or an alkaline earth metal, $R_2$ is halo or —O— dextran
$R_3$ is hydrogen, alkyl, phenyl, alkoxy phenyl, alkyl phenyl and

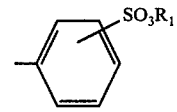

$Z_1$ is $[-H]_2$ or —CH=CH—CH=CH—
$Z_2$ is a nitrogen-nitrogen bond or a hydrogen attached to the nitrogen shown only,
Q is substituted or unsubstituted aryl where $Z_2$ is hydrogen or substituted or unsubstituted aryl-N= where $Z_2$ is a double bond, provided that the substituent groups aforesaid are other than halo or heavy metal wherein heavy metal is defined as a metal falling in periodic groups other than 1 or 2A, $m$ is 1 or 0 and $n$ is 1 or 2.

The adsorption of the albumin onto the support phase/CRD from the fluid containing it, is suitably carried out in a buffer of at least 0.05M molarity at a pH of between 6.5 and 8.5. While the process of the invention is not limited thereto and any method of contacting is considered within the scope of the invention, it is considered convenient to charge the suspension of the support phase/CRD composition to a chromatographic column and to pass through said column, the substantially cell free albumin containing fluid. The eluate is substantially albumin free and may be further processed as desired.

The albumin is then removed from the support phase/CRD suitably by eluting, preferably eluating a column, with a suitable eluent. The eluents may be selected from the group consisting of Chaotropes such as: aqueous Urea, aqueous quanidino-hydrochloride, buffered aqueous, lower alkanols, suitably buffered aqueous ethanol and aqueous thiocyanate in association with any cation giving rise to sufficient solubility. Alkanoic acids suitably alkaline buffered alkanoic acids containing 2 to 10 carbon atoms and aqueous solutions containing certain cations, suitably those of potassium and the group 2A metals. The use of any of these eluents will provide a support phase/CRD composition of renewed activity which may be used to remove further amounts of albumin from additional charges of albumin containing fluids. However, where it is desired to isolate pure, non-denatured albumin the latter two groups of eluents, as well as aqueous thiocyanate solution should be employed. The albumin can then be isolated therefrom by, say, lyophilization in the usual manner.

DESCRIPTION OF THE PREFERRED EMBODIMENTS

In one embodiment of the present invention there may be employed as support phase agarose, preferably in the form of sepharose which may be in the form of packed sepharose (for example grades 2B, 4B or 6B) or cross-linked sepharose (for example, grades 2B, 4B, or 6B). As stated heretofore, the reactive dyes which may be utilized in the present invention possess certain common structural characteristics. Certain of these dyes may be more particularly identified by means of their Color Index generic name, Color Index constitution number, or commercial name. Among these dyes thus identified may be included the following: CI Reactive Orange 2 (CI Constitution No. 17865, also known as Cibacron Orange G-E, or Procion Brilliant Orange HGRS), CI Reactive Red 4 (CICN 18105, also known as Cibacron Brilliant Red 3B-A, or Procion Brilliant Red H7BS), CI Reactive Brown 1 (CICN 26440, also known as Cibacron Brown 3GR-A, or Procion Orange Brown HGS, CI Reactive Red 9 (CICN 17910, also known as Cibacron Scarlet 2G or Procion Scarlet H3GS). Of similar structure is CI Reactive Red 16, also known as Cibacron Scarlet 4G-B. Also included in this group are the anthraquinone dyes CI Reactive Blue 2 (CICN 61211, also known as Cibacron Blue F3G-A or Procion Blue HBS, and CI Reactive Blue 5 (CICN 61210, also known as Cibacron Brilliant Blue FBR-P).

Methods of making all of these dyes will be found in Pancharteck, et al., Col.Czech.Chem.Commune., 25, 2783 (1960).

Also within the scope of the present invention should be considered compounds wherein the terminal benzene sulfonic acid group is replaced by another substituent such as alkyl, phenyl, alkyl phenyl, alkoxy phenyl, hydrogen or the like. Typical of this group is CI Reactive Red (CICN 18159) (C. Calin, et al, Coloristica Buletin Informativ, 4, (No. 11, 1968) 179–200.

All of the foregoing dyes may be coupled with the support phase substrates by heating in water at moderately elevated temperatures, suitably above pH 6.0. In the preferred modification the mixtures are heated with stirring between 75° and 95°, the mixture cooled, and washed to remove the unbound dye.

The ratio of the weight of dye to the weight of support phase is not critical. Where too little dye is utilized the efficiency of the extractive process will be reduced in view of the presence of too few adsorption sites. If too much dye is used the product obtained is not only economically wasteful but problems of steric interference will arise which will actually serve to reduce the number of available adsorption sites for the albumin.

There may be utilized between 0.1 to 5 grams of dye per 4 grams of support phase. It is preferred however to utilize between 0.2 and 1 gram of dye per 4 grams of support phase. It should be noted however that from a practical point of view the support phase is not usually measured by weight but rather by volume of settled support phase in aqueous suspension. Thus, where the support phase is sepharose, 4 grams of sepharose would correspond substantially to 100 ml. of settled sepharose.

While the weight/volume ratio will of course vary with the chemical nature of the support phase and the size of the granules, within the scope of generally available support phases of the size represented by sepharose of grades 2B, 4B, and 6B, the foregoing ratios are sufficiently close to provide a satisfactory range of operability.

In the preferred modification of the coupling procedure, the dye, that is to say, between about 0.1 and 2 grams of dye, preferably between 0.2 and 1 grams of dye, is dissolved or suspended in a small amount of water, between 10 and 50 ml. is generally suitable, and added to 100 ml. (measured as settled support phase of support phase, in water. The amount of water to suspend the support phase is not critical; between 100 ml. and 1000 ml. have been found suitable. The mixture is gently agitated and warmed to below the boiling point of water. A temperature range of 75° thru 95° C has been found satisfactory. The pH of the solution is maintained slightly above pH 6, suitably between pH 6 and pH 8 by the addition of either aqueous alkali or a buffer. The actual reaction time will depend upon the dilution of the dye, the temperature, and the agitation of the support phase. Nevertheless, the reaction can generally be considered to be complete in between from about 5 to about 60 minutes. The coupled product (designated herein SP/CRD) is then separated from the aqueous phase, suitably by decantation and washed to remove any unreacted dye. It has been found suitable to wash thoroughly with water at ambient temperature followed by a suitable salt, such as guanidine hydrochloride (5M) which will remove any unbound dye. The use of guanidine hydrochloride solution is not critical and other washes may also be used.

The thus purified SP/CRD is then suspended in a buffer, suitably a buffer of between a pH of 6.5 and 8.5. The albumin adsorptive capacity of the product thus produced will of course depend upon the dye/support phase ratio. However, products produced in accordance with the foregoing procedures will have an absorptive capacity of the order of 30 milligrams of albumin per ml. of settled SP/CRD.

It should be borne in mind that different dyes will react at different rates with different support phases. Furthermore care must be taken that the support phase does not become physically changed, i.e., by partial or complete melting, during the coupling process. For example, it should be noted that while Cibacron Blue F-3GA reacts very rapidly with sepharose at 80° C, other dyes will couple slowly with ordinary sepharose at this temperature. While at 90° coupling occurs rapidly, the product produced is, although operative, not of optimum physical characteristics. Thus, where higher reaction temperatures are required, it is desirable to utilize cross-linked support phases such as cross-linked sepharose.

As examples of other support phases which may be utilized in the process of the present invention, there may be mentioned polyacryamide gels, and acrylic resins containing amino groups, such as, for example, Amberlite ®IRC 45.

Also included within the scope of the present invention are the Dextran derivatives of Cibacron Blue F3GA and Cibacron Brilliant Blue FBR-P. In these dyes the chloro group of the triazine moiety is replaced by an —O— linkage to a Dextran molecule. The former when coupled with Dextran 2000 yields Blue Dextran 2000 ®.

The foregoing coupling procedures for the formation of SP/CRD depend upon the reaction of a halo group on the triazine moiety with a labile group on the support phase. Such reaction is not feasible where this group has been replaced by a —O—Dextran linkage. Nevertheless, where the CRD possesses a labile amino group such as, for example, the primary amino group on the anthraquinone moiety of Cibacron Blue F3GA and Cibacron Brilliant Blue FBR-P, coupling may be carried out by the cyanogen bromide method of Cuatracasas. In this procedure, the support phase is activated by treatment with aqueous alkaline cyanogen bromide and the suitably buffered support phase reacted with the dye. In this procedure the Dextran/CRD in a similar buffer is then added to the activated support phase and coupling allowed to proceed. The coupling reaction may take place at temperatures between 0° C and ambient temperature, however, it is preferred to carry out the reaction at approximately 4° C for approximately 24 hours. After elapse of this time, the conjugate is successively washed with aqueous sodium bicarbonate (pH approximately 9.5), concentrated aqueous urea (approximately 6M), water, and a high ionic strength buffer of pH between 6.5 and 8.5. It is preferred to utilize a tris-HCl/aqueous sodium chloride buffer. The sepharose/Dextran/CRD conjugate is then suspended in fresh buffer and may be stored at approximately 4° C until used.

In the practice of the albumin removal procedure it is found desirable to place the SP/CRD conjugate in a column in a high ionic strength buffer. The tris-HCl/sodium chloride buffer mentioned hereinabove has been found especially suitable. The high ionic strength of the buffer system is important for the operation of the procedure since it prevents the SP/CRD from acting as a cationic exchange column. It has been found suitable to apply aproximately 2 ml. of albumin containing plasma to approximately 10 ml. of settled SP/CRD. The plasma is then run through the column and the column washed with the aforementioned buffer. Elution was followed by uv adsorption of the eluate.

As stated heretofore the critical factor in this procedure is the ionic strength of the buffer system. In order to be operative the buffer should have an ionic strength of at least 0.05M, no upper limit being necessary, at a pH of between 6.5 and 8.5, preferably a pH of about 8.0.

The thus obtained eluate is substantially albumin free and the remaining proteins may be isolated therefrom in methods known to the art. Examination and comparison of the initial plasma and the eluate shows that in addition to the albumin only small amounts of other proteins, principally, lipoproteins are removed.

The column may be regenerated by breaking the (SP/CRD)/Albumin bond. Where preservation of the albumin is not required an aqueous solution of urea or quanidine hydrochloride has been found suitable. The urea solution must be at least 1M, while solutions of 3M have been used, any strength up to saturation (ca 8M) is satisfactory. One column volume of urea solution is sufficient to break the bonds, however, 1–3 column volumes are usually employed.

Where it is desired to preserve the albumin an ethanol/aqueous alkali metal phosphate, suitable sodium phosphate solution is employed. The preferred volume ratio is 1:1 and the phosphate solution is between 0.05 and 0.1M at pH of 2.0–3, suitably 0.075M at pH 2.4, measured prior to mixing.

It has also been found that albumin may be eluted in high purity using an aqueous solution of thiocyanate together with, suitably the cations of sodium, potassium and group 2A metals which provides sufficient ionic strength. Especially suitable as cations are $Na^+$ and $K^+$. The ionic strength of these eluents should be, preferably, at least 0.05M. Lower concentrations cause tailing. Higher concentrations, say 0.1M to 1.0M bring a faster elution and are acceptable, these concentrations should not be considered as limiting, nevertheless much higher concentrations may adversely affect the purity of the albumin.

It has been found desirable to buffer the eluent, suitably to a pH between pH 6.0 and 9, most preferably to a pH of about 8. This is achieved by adding a buffer such as sodium bicarbonate or trishydrochloride to the eluent. An ionic strength of about 0.05–0.1M tris hydrochloride in the eluent has been found suitable.

It has also been found that basic buffered alkanoic acids are suitable as eluents. Acids containing 2–10 carbon atoms may be employed, acids containing 8–10 carbon atoms are preferred. Octanoic acid is especially suitable as it is the stabilizing agent of choice for albumin. Utilizing alkanoic acids, especially octanoic acid as an eluent, there is made available a stabilized solution of pure albumin which may, if desired, be concentrated under reduced pressure or lyophilized to provide pure buffered albumin.

Any buffer may be employed which will raise the pH of the solution to at least 6.5, pH 7.5–9 being an operative range, and about pH 8.0 being preferred. Tris hydrochloride/aqueous sodiumchloride is especially suitable as a buffer.

It should be noted that the solubility of $C_8$-$C_{10}$ alkanoic acids in water is not high. Octanoic acid has a solubility of the order of 4mM. Thus the preferred mode of preparing the eluent is to prepare a buffer such as tris hydrochloride (0.05–0.2M) suitably with 0.05–0.5M aqueous sodium chloride and add thereto as much of the alkanoic acid as will dissolve therein. Again, the solution should be buffered to at least pH 6.5, pH 7.5 – pH 9, being the operative range and a pH of about 8.0 being preferred.

Utilizing either method of column regeneration, the columns may be repeatedly utilized without loss of absorptive power.

DYES UTILIZED AS CRD'S

| CICN | CI Name | Trade Name(s) | Structural Formula |
|------|---------|---------------|--------------------|
| 17865 | CI Reactive Orange | Cibacron Orange G-E; Procion Brilliant Orange HGRS | *(structure)* |
| 61210 | CI Reactive Blue 5 | Cibacron Brilliant Blue FBR-P | *(structure)* |
| 61211 | CI Reactive Blue 2 | Cibacron Blue F3G-A; Procion Blue HBS | *(structure)* |
| 18105 | CI Reactive Red 4 | Cibacron Brilliant Red 3B-A; Procion Brilliant Red H7BS | *(structure)* |
| 26440 | CI Reactive Brown 1 | Cibacron Brown 3GR-A; Procion Orange Brown HGS | *(structure)* |
| 17910 | CI Reactive Red 9 | Cibacron Scarlet 2G; Procion Scarlet H3GS | *(structure)* |
| — | CI Reactive Red 16 | Cibacron Scarlet 4G-P | — |
| 18156 | CI Reactive Red 12 | Cibracon Brilliant Red B-A | *(structure)* |
| 18159 | CI Reactive Red 3 | — | *(structure)* |
| — | — | Blue Dextran | *(structure)* |
| — | — | — | *(structure)* |

EXAMPLE I 100 ml. of settled cross linked Sepharose ®4B (Pharmacia Fine Chemicals, Inc) is suspended in 250 ml. of water. 1 gm. of Cibacron ® Brilliant Blue FBR-P is dissolved in 25 ml. of water and the solution added to the sepharose suspension. The mixture is agitated gently and heated to 80° C for 45 minutes. The pH is held to at least pH 6 by addition of sodium bicarbonate or tris hydrochloride. The reaction mixture is cooled to ambient temperature, the supernatant liquid decanted and the solid phase washed thoroughly, first with water (3 1.) then with aqueous guanidine hydrochlorde solution (2 1., 5M.) and finally suspended in a mixed buffer of aqueous tris hydrochloride (0.05M) and aqueous sodium chloride (0.5M) (pH 8.0) to yield an SP/CRD conjugate of Sepharose 4B and Cibacron Brilliant Blue FBR-P.

In accordance with the above procedures, there may be utilized packed sepharose polyacrylamide gel and Amberlite ® IRC 45 to yield similar SP/CRD's.

In accordance with the procedures of the principle example, but using as CRD's, Procion Brilliant Orange HGRS, Procion Blue HBS, Procion Brilliant Red H7B5, Procion Orange Brown HGS, Procion Scarlet H3GS, Cibacron Scarlet 4GP and Cibacron Brilliant Red BA, and as SP utilizing a cross-linked sepharose, polyacrylamide gel or a polyacrylic amino group containing resin similar SP/CRD's are obtained provided the temperature of reaction is raised to 90°–95° C.

EXAMPLE II

Preparation of Sepharose-Blue Dextran Conjugate 100 ml. of settled Sepharose 4B (Pharmacia Fine Chemicals Inc) is treated with an aqueous solution of cyanogen bromide (16g) at pH 11.0 and 10° C for 5 hours. After completion of the reaction the supernatant liquid is removed by decantation and the sepharose agitated with sodium bicarbonate buffer (0.1M, pH 9.5). The supernatant liquid is again removed by decantation and Blue Dextran (1g) in 100 ml. of aqueous sodium bicarbonate, (0.1M, pH 9.5) is added. The reagents are allowed to stand for 24 hours at 4° C. The supernatant liquid is then removed by decantation and the product washed successively with aqueous sodium bicarbonate (4 l, 0.1M, pH 9.5), aqueous urea (4 l., 6M), water (4 l.) and a mixed buffer consisting of aqueous tris-hydrochloride (0.05M) and aqueous sodium chloride (0.5M) (4 l., pH 8.0). After removal of the supernatant wash of this last buffer, the thus produced SP/CRD is suspended in a similar solution and, if desired, stored at 4° C.

EXAMPLE III

Removal of Albumin from Plasma

A chromatographic column (1.0 × 20 cm) is charged with circa 10 ml. of SP/CRD produced in accordance with Example II suspended in the aforementioned tris-hydrochloride/sodium chloride buffer. 2 ml. of plasma is applied to the column and eluted with buffer until no further protein was eluted. This is checked by ultra-violet examination of the eluate wherein $A_{280}$ is less than 0.020. The eluate is then reduced in volume by diaflowing (utilizing an Amicon-UM10 membrane) to a volume of 2 ml.

The procedure was controlled by running control samples through a Sepharose 4B column which had not been conjugated with Blue Dextran. The diaflowed eluate is then subjected to assay by cellulose acetate membrane electrophoresis to yield the results set forth in Table I.

TABLE I

Recovery of Plasma Protein Fractions After Passage Through Sepharose-Blue Dextran

| Fraction | Control Plasma (grams/100 ml.) | SBD-Treated Plasma | % Recovery |
| --- | --- | --- | --- |
| Albumin | 4.10 | 0.16 | 4 |
| Alpha-1 | 0.17 | 0.16 | 94 |
| Alpha-2 | 0.72 | 0.60 | 84 |
| Beta | 0.67 | 0.65 | 96 |
| Gamma | 0.95 | 0.93 | 98 |
| Total Protein | 6.61 | 2.50 | 38 |

Fractions were quantitatively assayed after cellulose acetate membrane electrophoresis as described in text. Total protein was determined by the method of Lowry, et al, (J. Biol. Chem. 193, 265 (1951)).

EXAMPLE IV

Removal of Albumin from Plasma

A chromatographic column (1.0 × 20 cm) is charged with circa 10 ml. of SP/CRD produced in accordance with Example I utilizing as SP, cross linked Sepharose 4B and as CRD, Procion Brilliant Red H7BS, suspended in the aforementioned tris-hydrochloride/sodium chloride buffer. 2 ml of plasma is applied to the column and eluted with buffer until no further protein was eluted. This is checked by ultraviolet examination of the eluate wherein $A_{280}$ is less than 0.020. The eluate is then the aforementioned tris-sodium chloride buffer.

EXAMPLE V

Removal of Albumin from Plasma

A chromatographic column (5 × 100 cm) is charged with circa 1000 ml of SP/CRD produced in accordance with Example I utilizing as SP, cross linked Sepharose 4B and as CRD, Cibacrom Blue F3GA, suspended in the aforementioned tris-hydrochloride/sodium chloride buffer. 600 ml of plasma is applied to the column and eluted with buffer until no further protein was eluted. This is checked by ultraviolet examination of the eluate wherein $A_{280}$ is less than 0.020. The eluate is then the aforementioned tris-sodium chloride buffer.

EXAMPLE VI

Regeneration of Column with Albumin Recovery

The albumin containing column of Example V is washed with an aqueous eluent comprising sodium thiocyanate (0.3M) and tris-hydrochloride (0.05M, pH8) until no further albumin is shown to be present in the eluate by optical density monitoring.

The eluate is then dialyzed against distilled water using an Amicon DC-52 hollow fiber. The dialysis is continued until the wash water has a conductivity of less than 50 micro-mho and is negative in the ferric chloride test indicating removal of the thiocyanate.

The dialysis residue is then concentrated and lyophilized to yield albumin of purity exceeding 98%.

In accordance with the above procedure any of the SP/CRDS produced in accordance with Examples I and II may be employed. In accordance with the above procedures in place of sodium thiocyanate, the cation may be ammonium, potassium or any group 2A metal giving rise to a sufficient solubility to reach the required concentration range.

EXAMPLE VII

Column Regeneration

The column which was eluted in accordance with Example VI is prepared for reuse by washing with saline tris-hydrochloride buffer ($N_aCl$ 0.05M, Tris-HCl 0.05M, pH 8.0).

We claim:

1. A method of obtaining albumin from substantially cell free aqueous fluids containing the same comprising the steps of
a. suspending a composition of the general formula $(SP)_x(CRD)$ wherein CRD is a color reactive dye of the general formula

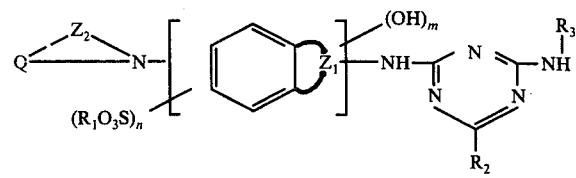

wherein
R₃ is hydrogen, alkyl, phenyl, alkoxy phenyl, alkyl phenyl or

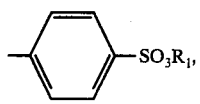

wherein $R_1$ is hydrogen, an alkali metal, or an alkaline earth metal, $R_2$ is halo or —O—dextran,
$Z_1$ is two hydrogen atoms, or —CH═CH—CH═CH— to form a naphthyl nucleus with the phenyl nucleus to which it is attached,
$Z_2$ is one bond of a nitrogen-nitrogen bond or a hydrogen attached to the nitrogen shown only,
Q is substituted or unsubstituted aryl where $Z_2$ is hydrogen, or Q is substituted or unsubstituted aryl-N═ where $Z_2$ is one bond of a double bond,
m is 1 or 0, n is 1 or 2, provided that the substituent groups aforesaid are other than halo or heavy metal, and wherein SP is a solid support phase selected from the group consisting of agarose, polyacrylamide and acrylic resin containing amino groups, provided that where the CRD, $R_2$ is halo, the SP- linkage in the (SP)ₓ-(CRD) is to the $R_2$ bearing position of the triazine moiety, and where in the CRD $R_2$ is O-dextran, the SP- linkage in the (SP)ₓ-(CRD) is to the Q moiety,
and x is expressed as a weight ratio between 0.8 and 40,
in a buffer of at least 0.05 M molarity at a pH of between 6.5 and 8.5;
b. contacting said suspension with said albumin containing fluid to provide a suspension having albumin absorbed upon the solid phase thereof;
c. separating the solid phase-albumin adsorbate from the aqueous phase by treating the solid phase-albumin adsorbate with an aqueous ionic eluent wherein the anion is thiocyanate.

2. A method of claim 1 wherein SP/CRD has the general formula

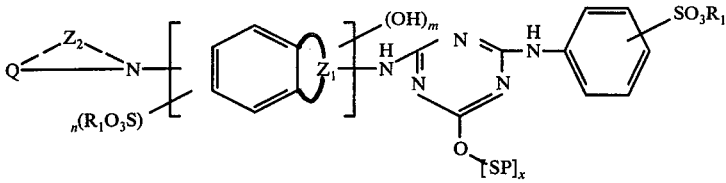

wherein x, Q, $Z_1$, $Z_2$, and $R_1$ are defined as in claim 1.

3. A method of claim 2 wherein SP is sepharose.

4. A method of claim 2 wherein SP is a polyacrylamide gel.

5. A method of claim 2 wherein SP is an acrylic resin containing amine groups.

6. A method of claim 1 wherein SP/CRD has the general formula

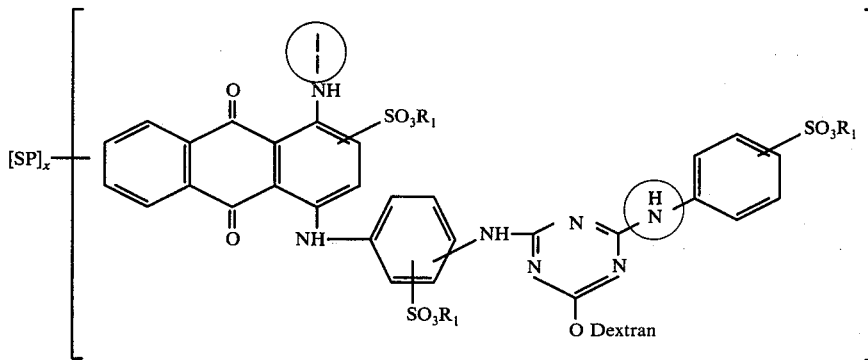

x, and $R_1$ are as defined in claim 1.

7. A method of claim 6 wherein SP is sepharose.

8. A method of claim 6 wherein SP is a polyacrylamide gel.

9. A method of claim 6 wherein SP is an acrylic resin containing amino groups.

10. A process according to claim 3 wherein CRD is Procion Blue HBS or Cibacron Brilliant Blue FBR-P.

11. A process according to claim 3 wherein CRD is Procion Orange Brown HGS, Procion Brilliant Red H7BS, Procion Scarlet H3GS, Procion Brilliant Orange HGRS.

12. A method according to claim 1 wherein the eluent comprises a cation of a metal of group 2A of the periodic table, sodium or potassium and also a basic buffer.

13. A method of claim 1 wherein the thiocyanate has a concentration of between 0.1M and 1.0M.

14. A method in accordance with claim 12 wherein the eluent is an aqueous solution of sodium thiocyanate and a basic buffer.

15. A process of claim 1 additionally comprising the step of isolating the albumin by dialysis against water.

16. A process of claim 15 wherein the dialysis is carried out against distilled water to a conductivity below 50μmhos, said water giving a negative result in the ferric chloride test for thiocyanate.

17. A process of claim 16 further comprising removal of water from the dialysate containing the albumin.

18. A process of claim 17 wherein the water is removed by concentration and lyophilization.

19. A method of removing albumin from aqueous fluids containing the same comprising
i. the method of claim 1
ii. treating the thus produced solid phase-albumin adsorbate with an aqueous eluent comprising thiocyanate anions and cations selected from the group consisting of cations of groups 2A metals sodium and potassium, said eluent further comprising a basic buffer, iii. separating the thus formed albumin free solid phase from the liquid phase,
iv. utilizing said albumin free solid phase in step (a) of claim 1,
v. repeating steps (i) thru (iv) hereof.

* * * * *